United States Patent
Tsujimoto

(10) Patent No.: US 10,905,597 B2
(45) Date of Patent: Feb. 2, 2021

(54) CONVEYING DEVICE AND METHOD FOR MANUFACTURING DISPOSABLE WEARABLE ARTICLE USING SAME

(71) Applicant: ZUIKO CORPORATION, Osaka (JP)

(72) Inventor: Yoshiaki Tsujimoto, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 127 days.

(21) Appl. No.: 16/315,002

(22) PCT Filed: Jul. 13, 2016

(86) PCT No.: PCT/JP2016/070658
§ 371 (c)(1),
(2) Date: Jan. 3, 2019

(87) PCT Pub. No.: WO2018/011905
PCT Pub. Date: Jan. 18, 2018

(65) Prior Publication Data
US 2019/0247240 A1 Aug. 15, 2019

(51) Int. Cl.
*A61F 13/49* (2006.01)
*B65H 5/00* (2006.01)
(Continued)

(52) U.S. Cl.
CPC .. *A61F 13/15764* (2013.01); *A61F 13/15739* (2013.01); *A61F 13/15747* (2013.01);
(Continued)

(58) Field of Classification Search
CPC ......... A61F 13/49; B65G 47/244; B65H 5/12; B65H 2801/57
See application file for complete search history.

(56) References Cited

U.S. PATENT DOCUMENTS

| 4,191,303 A | * | 3/1980 | Kinghorn, Sr. | ........ B65D 88/42 220/222 |
| 5,480,226 A | * | 1/1996 | Milstead | ............. E01C 19/1036 34/137 |

(Continued)

FOREIGN PATENT DOCUMENTS

| CN | 101018722 | 8/2007 |
| CN | 101087575 | 12/2007 |

(Continued)

OTHER PUBLICATIONS

Office Action dated Mar. 26, 2020 in corresponding Chinese Patent Application No. 201680087572.5 with English-language translation.

(Continued)

*Primary Examiner* — Andrew M Tecco
*Assistant Examiner* — Eyamindae C Jallow
(74) *Attorney, Agent, or Firm* — Wenderoth, Lind & Ponack, L.L.P.

(57) ABSTRACT

A conveying device comprises: a plurality of holding mechanisms attached to a rotary shaft; a speed-changing mechanism which changes the angular speed of each of the plurality of holding mechanisms; a first cover extending from a first holding mechanism toward a second holding mechanism, such that the first cover covers a gap between the two holding mechanisms from an outside thereof in a radial direction of the rotating shaft; and a second cover extending from the second holding mechanism toward the first holding mechanism such that the second cover covers the gap from the outside thereof in the radial direction, and overlapping with the first cover. The two covers have lengths enough to be able to overlap with each other in the radial direction in a state in which the two holding mechanisms are furthest apart from each other.

17 Claims, 7 Drawing Sheets

(51) Int. Cl.
    B65G 47/244    (2006.01)
    A61F 13/15     (2006.01)
    B65G 47/248    (2006.01)
    B65H 5/12      (2006.01)

(52) U.S. Cl.
    CPC ............ *B65G 47/248* (2013.01); *B65H 5/12* (2013.01); *B65G 2201/0229* (2013.01); *B65H 2701/19* (2013.01)

(56) References Cited

U.S. PATENT DOCUMENTS

| | | | |
|---|---|---|---|
| 2002/0125105 A1* | 9/2002 | Nakakado | B65G 47/244 198/471.1 |
| 2007/0074953 A1* | 4/2007 | McCabe | B65G 47/848 198/377.08 |
| 2007/0193856 A1 | 8/2007 | McCabe | |
| 2008/0023296 A1* | 1/2008 | Aoyama | B65G 47/848 198/468.2 |
| 2008/0099130 A1 | 5/2008 | Umebayashi et al. | |
| 2008/0196564 A1* | 8/2008 | McCabe | B26D 1/425 83/23 |
| 2010/0300838 A1 | 12/2010 | McCabe | |
| 2011/0209270 A1 | 9/2011 | Carlson et al. | |
| 2013/0152360 A1* | 6/2013 | Schoultz | A61F 13/15756 29/428 |
| 2013/0270067 A1* | 10/2013 | Papsdorf | B65G 47/848 198/377.01 |
| 2014/0115757 A1* | 5/2014 | Umebayashi | A61F 13/492/400 |
| 2014/0274646 A1* | 9/2014 | Schneider | A61F 13/15756 493/379 |
| 2015/0083848 A1* | 3/2015 | Yanez, Jr. | B65H 23/032 242/615 |
| 2015/0192493 A1* | 7/2015 | Kouji | G01N 21/909 356/240.1 |
| 2015/0223992 A1 | 8/2015 | Maehara et al. | |
| 2018/0362266 A1* | 12/2018 | Schneider | B65G 47/244 |

FOREIGN PATENT DOCUMENTS

| | | |
|---|---|---|
| CN | 103635168 | 3/2014 |
| EP | 1 820 757 | 8/2007 |
| EP | 1 961 403 | 8/2008 |
| JP | 2005212149 | 8/2005 |
| JP | 4054191 | 12/2007 |
| WO | 2010/050867 | 5/2010 |
| WO | 2014/006834 | 1/2014 |

OTHER PUBLICATIONS

Extended European Search Report dated Mar. 18, 2019 in European Patent Application No. 16908809.3.
International Search Report dated Aug. 30, 2016 in International (PCT) Application No. PCT/JP2016/070658.

* cited by examiner

CONVEYING DEVICE AND METHOD FOR MANUFACTURING DISPOSABLE WEARABLE ARTICLE USING SAME

TECHNICAL FIELD

The present invention relates to a conveying device for conveying a conveyance target member to be conveyed.

BACKGROUND ART

A heretofore-known conveying device as described, for example, in the following Patent Literature 1, comprises a rotary shaft, a plurality of holding mechanisms (revolving sections) attached to the rotary shaft in a manner rotatable in response to rotation of the rotary shaft and each configured to hold a conveyance target member (workpiece), and a speed-changing mechanism (speed-changing section) operable, during a period of time when each of the holding mechanisms rotates about the rotary shaft, to change the angular speed of the holding mechanism.

The plurality of holding mechanisms are arranged at respective positions having different angles about the rotary shaft. The speed-changing mechanism is configured to change respective angular speeds of mutually adjacent two of the plurality of holding mechanisms, such that an angular difference arises between the two holding mechanisms. Thus, a distance between the two holding mechanisms changes according to a difference between the angular speeds of the two holding mechanisms.

Here, if foreign matter such as mote or dust enters a gap between the mutually adjacent two holding mechanisms, the foreign matter is likely to exert a negative influence on a mechanism (e.g., a mechanism supporting the holding mechanisms in a manner rotatable about the rotary shaft) provided between the two holding mechanisms, thereby causing the conveying device to fail to operate normally.

Therefore, the conveying device described in the Patent Literature 1 is equipped with a cover attached to the mutually adjacent two holding mechanisms, such that it covers the gap between the two holding mechanisms from an outside thereof in a radial direction of the rotary shaft. This cover is formed in an accordion-like structure capable of stretching and contracting in response to a change in the distance between the mutually adjacent two holding mechanisms.

However, in the case where the accordion-shaped cover is provided between the two holding mechanisms, there is a possibility that, when the two holding mechanisms come close to each other, the cover fails to be folded in an expected manner, and part of the cover protrudes inwardly or outwardly in the radial direction of the rotary shaft.

As a result, the cover is likely to be damaged due to contact with a surrounding component, resulting in failing to effectively fulfill a cover function.

CITATION LIST

[Parent Document]
Patent Literature 1: JP 4054191B (particularly FIG. 3)

SUMMARY OF INVENTION

It is an object of the present invention to provide a conveying device capable of effectively preventing foreign matter from entering a gap between mutually adjacent two holding mechanisms, irrespective of a distance between the two holding mechanisms, and a method for manufacturing a disposable wearable article using the conveying device.

In order to solve the above problem, the present invention provides a conveying device for conveying a conveyance target member to be conveyed. The conveying device comprises: a rotary shaft; a plurality of holding mechanisms attached to the rotary shaft in a manner rotatable in response to rotation of the rotary shaft and each capable of holding the conveyance target member, wherein the plurality of holding mechanisms are arranged at respective positions having different angles about the rotary shaft; a speed-changing mechanism which changes an angular speed of each of the plurality of holding mechanisms such that an angular difference arises between mutually adjacent two of the plurality of holding mechanisms; a first cover extending from a first holding mechanism which is one of the two holding mechanisms, toward a second holding mechanism which is a remaining one of the two holding mechanisms, such that the first cover covers a gap between the two holding mechanisms from an outside thereof in a radial direction of the rotating shaft; and a second cover extending from the second holding mechanism toward the first holding mechanism such that the second cover covers the gap from the outside thereof in the radial direction, and overlapping with the first cover in the radial direction, wherein the first cover and the second cover have respective lengths enough to be able to overlap with each other in the radial direction, in a state in which the two holding mechanisms are furthest apart from each other.

The present invention makes it possible to effectively prevent foreign matter from entering a gap between the mutually adjacent two holding mechanisms, irrespective of a distance between the two holding mechanisms.

DESCRIPTION OF EMBODIMENTS

With reference to the accompanying drawings, an embodiment of the present invention will now be described. It should be understood that the following embodiment is a specific example of the present invention, and is not intended to restrict a technical scope of the present invention.

Figure 1:
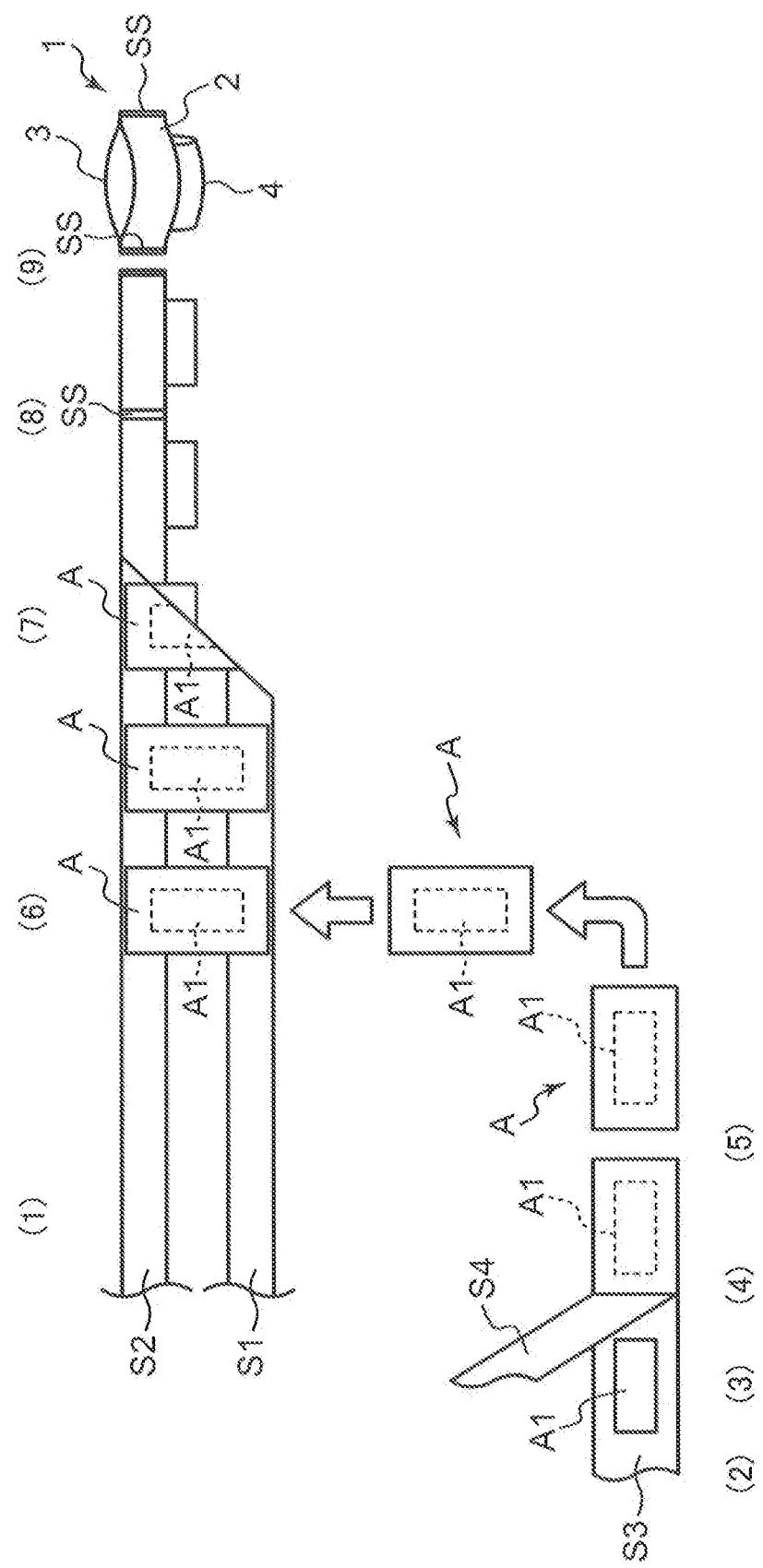
FIG. 1 is a schematic process diagram depicting a disposable diaper manufacturing method according to the present invention.

FIG. 1 is a process diagram depicting a manufacturing method for a disposable diaper 1 as one example of a disposable wearable article, according to the present invention.

The disposable diaper 1 comprises a front abdominal portion (waist portion) 2 to be disposed on the front side of the abdominal region of a wearer, a rear dorsal portion (waist portion) 3 to be disposed on the side of the hip region of the wearer, and a crotch portion 4 to be disposed on a crotch region of the wearer.

Each of opposite ends of the front abdominal portion 2 and a corresponding one of opposite ends of the rear dorsal portion 3 are bonded together by a side seal SS. Further, each of the front abdominal portion 2 and the rear dorsal portion 3 is stretchable. Specifically, each of the front abdominal portion 2 and the rear dorsal portion 3 may be prepared by forming it using a material having elasticity in itself (elastic nonwoven fabric) or by attaching an elastic member between a pair of sheets made of a nonwoven fabric, in a stretched state. The elastic member may be formed of polyurethane, natural rubber or thermoplastic resin. Further, the elastic member may be formed into a string-like shape or a ribbon-like shape.

The crotch portion 4 is bonded to the front abdominal portion 2 and the rear dorsal portion 3, such that the crotch portion 4 extends between the front abdominal portion 2 and the rear dorsal portion 3.

The crotch portion 4 in this embodiment is composed of an absorbent body A capable of absorbing a bodily fluid, such as urine, of the wearer. Specifically, the absorbent body A comprises: a liquid-permeable top sheet S4 provided on the side of the skin of the wearer, a cover sheet S3 provided on a side opposite to the skin of the wearer; an absorbent core A1 provided between the two sheets S3, S4. A bodily fluid penetrating through the top sheet S4 is absorbed by the absorbent core A1. Here, the top sheet S4 may be formed of a non-woven fabric or mesh sheet permitting penetration of liquid. The cover sheet S3 may be formed using a polyethylene film having breathability (air permeability), a nonwoven fabric having water repellency and breathability, or a laminated film thereof. Further, the absorbent core A1 may be formed by laminating fluffs obtained by subjecting roll pulp to crushing and fibrillation. In this case, a superabsorbent polymer may be mixed in the fluffs.

In this embodiment, the crotch portion 4 is composed of the absorbent body A. However, the configuration of the crotch portion 4 is not limited thereto. For example, it is possible to employ a crotch portion 4 from which the absorbent core A1 is omitted.

Further, although this embodiment has been described based on the disposable diaper 1 in which the front abdominal portion 2 and the rear dorsal portion 3 are composed of separate members, respectively, the configuration of the disposable diaper is not limited thereto. For example, it is possible to form two leg holes in a sheet having an area corresponding to the front abdominal portion 2 and an area corresponding to the rear dorsal portion 3, and utilize an area of the sheet between the leg holes, as the crotch portion 4. In this case, the absorbent body A may be bonded to the area of the sheet between the leg holes.

With reference to FIG. 1, a manufacturing method for the disposable diaper 1 will be described below.

The manufacturing method for the disposable diaper 1 comprises a waist sheet conveying step (1), a crotch sheet conveying step (2), a core bonding step (3), a sheet bonding step (4), an absorbent body cut-out step (5), an absorbent body bonding step (6), a half-folding step (7), a side seal forming step (8), and a cutting step (9).

In the waist sheet conveying step (1), a front sheet (waist sheet) S1 for forming the front abdominal portion 2 and a rear sheet (waist portion) S2 for forming the rear dorsal portion 3 are conveyed along a longitudinal direction of these sheets. The conveyance direction of the front sheet S1 and the conveyance direction of the rear sheet S2 are parallel to each other. The waist sheet conveying step (1) is performed under the condition that a given tension is applied to each of the front sheet S1 and the rear sheet S2, until the cutting step (9) which will be described later is completed.

In the crotch sheet conveying step (2), the cover sheet S3 is conveyed along a longitudinal direction of this sheet. The conveyance direction of the cover sheet S3 is parallel to the conveyance directions of the front sheet S1 and the rear sheet S2. The crotch sheet conveying step (2) is performed under the condition that a given tension is applied to the cover sheet S3, until the absorbent body cut-out step (5) which will be described later is completed.

In the core bonding step (3), a plurality of the absorbent cores A1 are sequentially bonded onto the cover sheet S3.

In the sheet bonding step (4), the top sheet S4 is disposed on the cover sheet S3 such that each of the absorbent cores A1 is sandwiched between the cover sheet S3 and the top sheet S4, and the top sheet S4 is bonded to the cover sheet S3 to form a continuous body (its reference sign is omitted) consisting of a series of the absorbent bodies A.

In the absorbent body cut-out step (5), a laminate of the cover sheet S3 and the top sheet S4 is cut at a position between adjacent two of the absorbent cores A1 to cut out and separate each of the absorbent bodies A from the continuous body.

In the absorbent body bonding step (6), the cut-out absorbent body (crotch member) A is turned 90 degrees and then conveyed to a position where the absorbent body A extends between the front sheet S1 and the rear sheet S2, and one end and the other end of the absorbent body A are bonded, respectively, to the front sheet S1 and the rear sheet S2 to form a bonded body (its reference sign is omitted).

In the half-folding step (7), the bonded body is half-folded in a width direction orthogonal to the longitudinal direction of each of the two sheets S1, S2.

In the side seal forming step (8), each of two sets of superimposed areas of the two sheets S1, S2 located, respectively, on both sides of the absorbent body A in the longitudinal direction of the each of the two sheets S1, S2, are bonded together to form a side seal SS.

In the cutting step (9), the two sheets S1, S2 are cut such that the side seal SS is left on each of the both sides of the absorbent body A in the longitudinal direction of each of the two sheets S1, S2, to form the disposable diaper 1.

In the above manufacturing method, a technique of conveying the front sheet S1 and the rear sheet S2 in parallel relation to each other and bonding the absorbent body A to the two sheets S1, S2 such that the absorbent body A extends between the two sheets S1, S2 is employed. However, the manufacturing method of the present invention is not limited thereto, For example, in the waist sheet conveying step (1), a waist sheet having two areas corresponding, respectively, to the front abdominal portion 2 and the rear dorsal portion 3 may be conveyed. In this case, by forming a plurality of leg holes in the waist sheet, an area corresponding to the crotch portion 4 may be formed as a part of the waist sheet between the leg holes. Then, in the absorbent body bonding step (6), the absorbent body A is bonded onto the area of the waist sheet between the leg holes.

Figure 2:
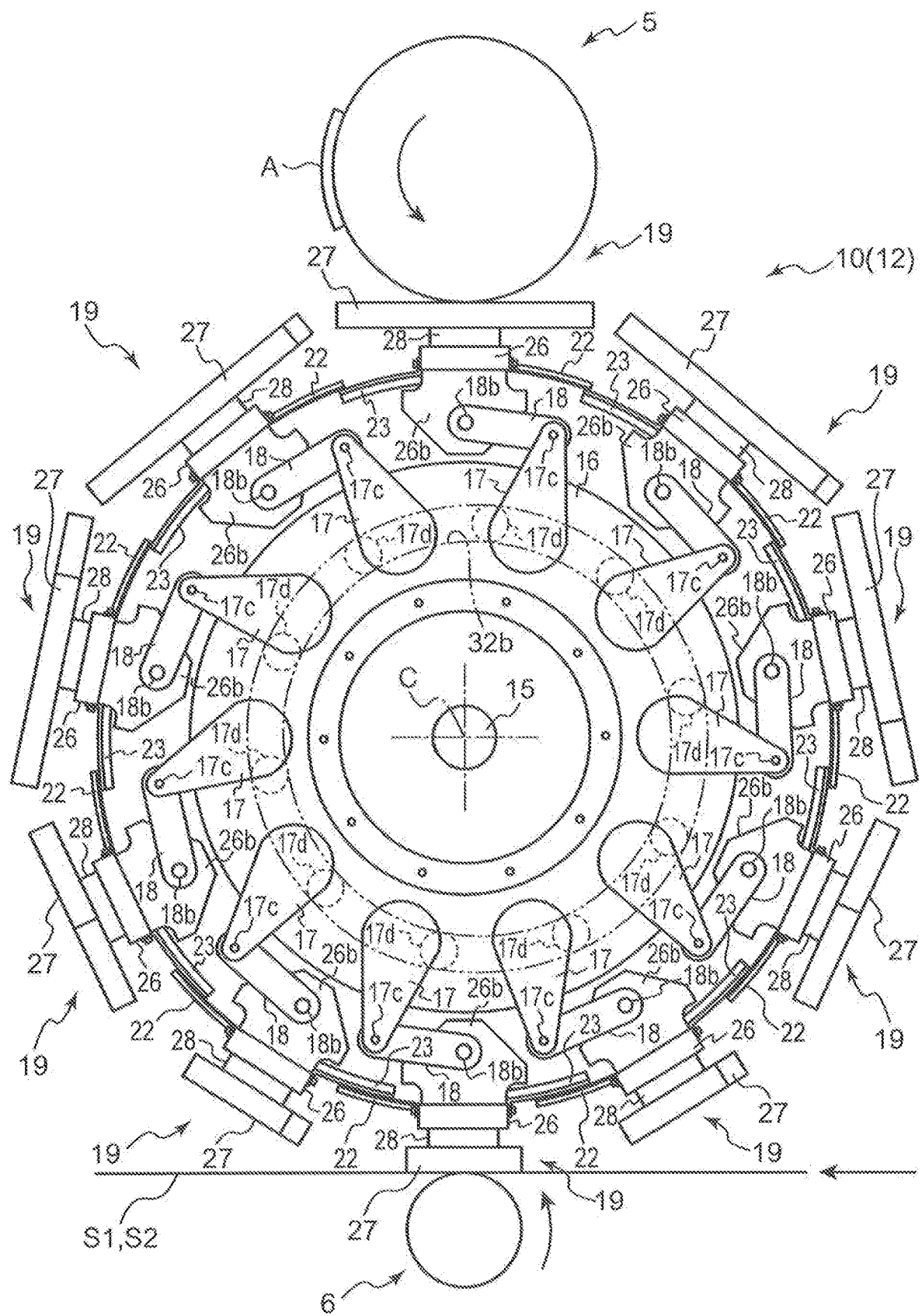
FIG. 2 is a front view depicting an entire configuration of a conveying device according to the present invention.

With reference to FIG. 2, a conveying device 10 to be used during the absorbent body bonding step (6) will be described below. FIG. 2 is a front view depicting an entire configuration of the conveying device 10.

The conveying device 10 is configured to receive, from a transfer roller 5, the absorbent body (conveyance target member) A held by the transfer roller 5 after being formed in the absorbent body cut-out step (5), and transfer the absorbent body A to the front sheet S1 and the rear sheet S2 each located between the conveying device 10 and a receiving roller 6 for guiding the two sheets S1, S2.

Further, the conveying device 10 is configured to turn the absorbent body A received from the transfer roller 5 by 90 degrees, and transfer the absorbent body A in the turned state to the receiving roller 6.

Figure 3:
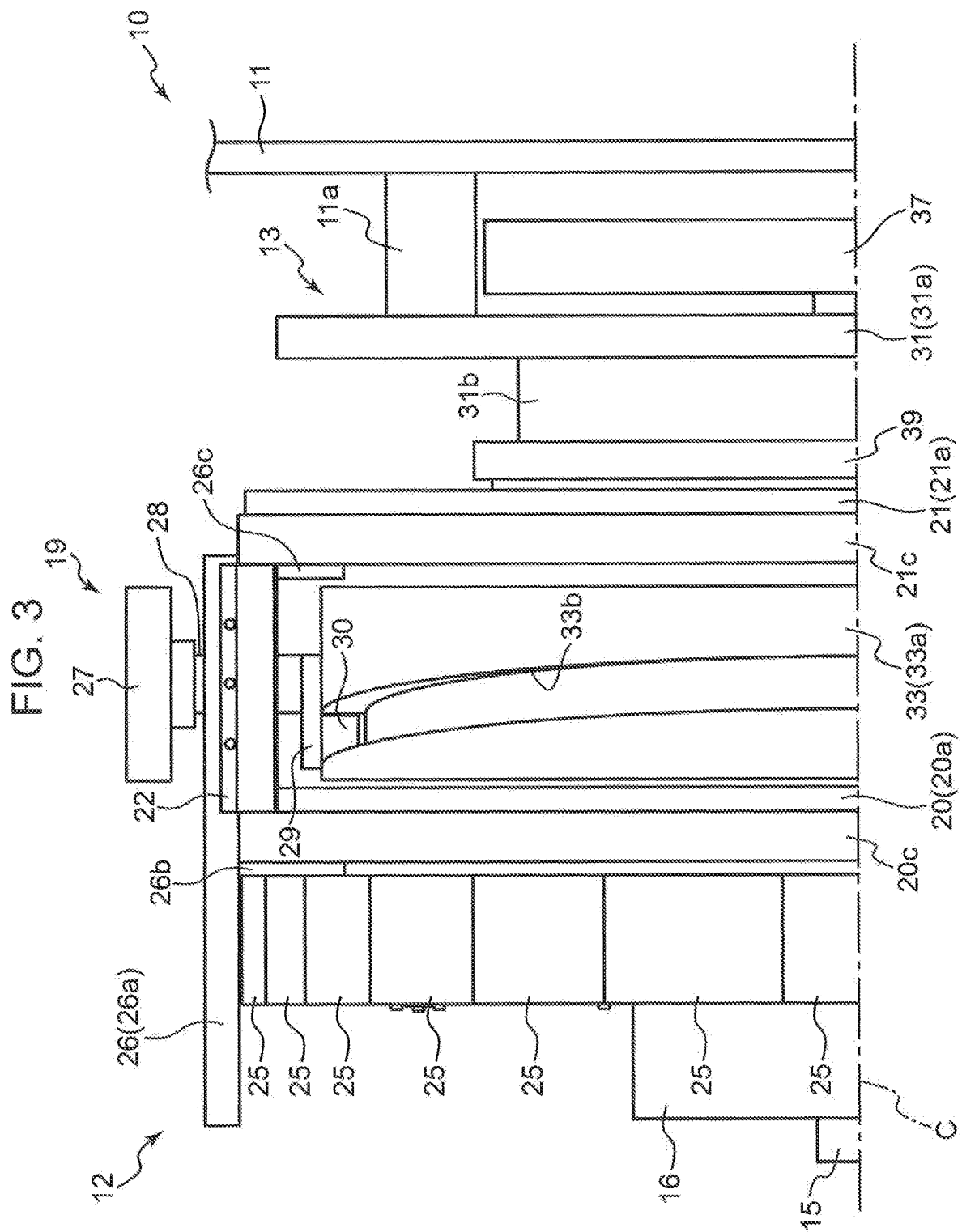
FIG. 3 is a side view enlargedly depicting a part of the conveying device in FIG. 2 in an absorbent body receiving zone.
Figure 4:
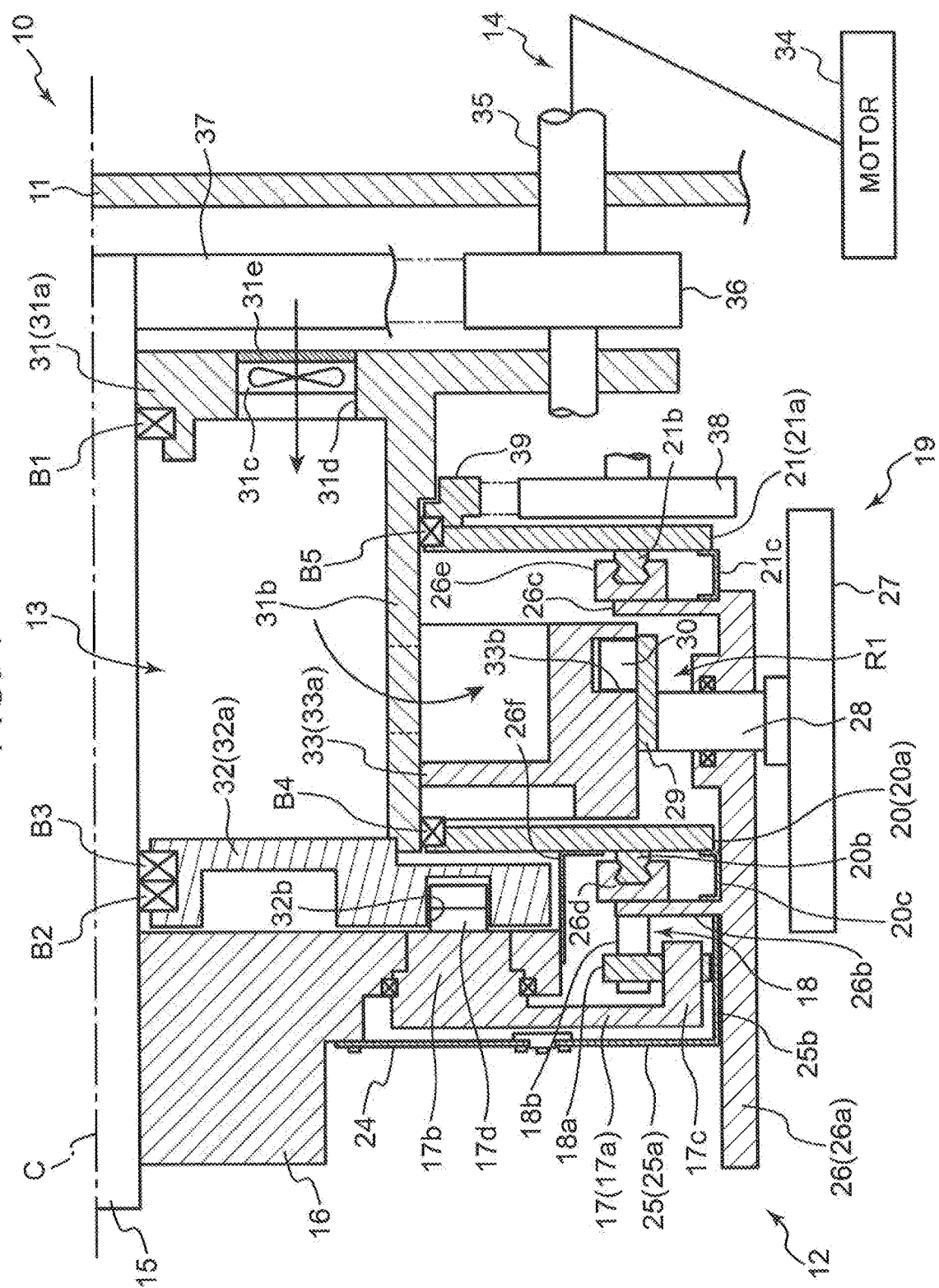
FIG. 4 is a side sectional view enlargedly depicting a part of the conveying device in FIG. 2 in an absorbent body transfer zone.

With reference to FIGS. 2 to 4, a specific configuration of the conveying device 10 will be described below. FIG. 3 is a side view enlargedly depicting a part of the conveying device in FIG. 2 in an absorbent body receiving zone, wherein some of the aftermentioned holding mechanisms 19 and the aftermentioned first and second covers 22, 23 attached thereto are omitted. FIG. 4 is a side sectional view enlargedly depicting a part of the conveying device in FIG. 2 in an absorbent body transfer zone.

The conveying device 10 comprises: a supporting plate 11; a rotary mechanism 12 attached to the supporting plate 11 in a manner rotatable about a rotation axis C; a stationary mechanism 13 fixed to the supporting plate 11, and a drive mechanism 4 (see FIG. 4) for rotationally driving the rotary mechanism 12 with respect to the supporting plate 11.

The stationary mechanism 13 comprises: a stationary drum 31 having a proximal end (end on the right side in FIGS. 3 and 4) fixed to the supporting plate 11 through a bracket 11a; a speed-changing cam 32 fixed to a distal end (end on the left side in FIGS. 3 and 4) of the stationary drum 31; and a turning cam 33 fixed to an outer peripheral surface of an intermediate portion of the stationary drum 31.

The stationary drum 31 has a bottom plate portion 31a disposed parallel to the supporting plate 11, and a cylindrical portion 31b protruding from the bottom plate portion 31a toward the distal end side. The cylindrical portion 31b is formed in a circular cylindrical shape having a center line aligned with the rotation axis C.

The speed-changing cam 32 has a cam body 32a fixed to a distal end of the cylindrical portion 31b such that it closes a distal-end-side opening of the cylindrical portion 31b, and a cam groove 32b provided in a surface of the cam body 32a facing the distal end side. The cam groove 32b is a groove opened toward the distal end side and having an approximately circular shape with a center at a position different from that of the rotation axis C of the rotary mechanism 12, in front view in FIG. 2.

The turning cam 33 has a cam body 33a fixed to an outer peripheral surface of the cylindrical portion 31b of the stationary drum 31, and a can groove 33b provided in an outer peripheral surface of the cam body 33a. The outer peripheral surface of the cam body 33a is a cylindrical surface having a center line aligned with the rotation axis C of the rotary mechanism 12, and the cam groove 33b is formed by depressing the outer peripheral surface of the cam body 33a. Further, the cam groove 33b has a region formed along a path whose position in a direction along the rotation axis C changes according to a change in position about the rotation axis C, as depicted in FIGS. 2 and 3.

The rotary mechanism 12 comprises a rotary shaft 15 supported by the stationary mechanism 13 in a manner rotatable about the rotation axis C. Specifically, the rotary shaft 15 penetrates through the bottom plate portion 31a of the stationary drum 31 and the cam body 32a of the speed-changing cam 32, while being supported by a bearing B1 in a manner rotatable with respect to the bottom plate portion 31a and further supported by two bearings B2, B3 in a manner rotatable with respect to the cam body 32a.

The rotary mechanism 12 further comprises ten holding mechanisms 19 attached to the rotary shaft 15 in a manner rotatable in response to rotation of the rotary shaft 15, and arranged at respective positions having different angles about the rotary shaft 15.

Additionally, the rotary mechanism 12 has the following configuration for supporting the holding mechanisms 19 in a manner rotatable in response to rotation of the rotary shaft 15.

Specifically, the rotary mechanism 12 comprises: a rotary supporting body 16 fixed to a distal end of the rotary shaft 15; ten arms 17 attached to the rotary supporting body 16; a link lever 18 attached to each of the arms 17 (i.e., ten link levers 18); and support members 20, 21 rotatably attached to the stationary drum 31.

The rotary supporting body 16 is a disk-shaped member provided on the distal side with respect to the turning cam 33.

Each of the arms 17 has an arm body 17a attached to an outer peripheral edge of the rotary supporting body 16 and the link lever 18, and a cam follower 17d extending from the arm body 17a toward the proximal end side (right side in FIG. 4) of the arm body 17a and inserted into the cam groove 32b of the speed-changing cam 32. The arm body 17a has a first end attached to the rotary supporting body 16 in a manner rotatable about a pivot 17b, and a second end attached to the link lever 18 in a manner rotatable about a pivot 17c. Each of the pivots 17b, 17c extends parallel to the rotation axis C. The can follower 17d is attached to the arm body 17a in a manner rotatable about a pivot parallel to the rotation axis C. This pivot is disposed at a position different from the pivot 17b, in front view in FIG. 2. Thus, when the position of the cam follower 17d within the cam groove 32b is changed during rotation of the rotary shaft 15, the arm body 17a is rotated about the pivot 17b with respect to the rotary supporting body 16.

The link lever 18 has a lever body 18a attached to the arm 17 and the holding mechanism 19. The lever body 18a has a first end attached to the arm body 17a in a manner rotatable about the pivot 17c, and a second end attached to the holding mechanism 19 in a manner rotatable about a pivot 18b. The pivot 18b extends parallel to the rotation axis C.

With reference to FIGS. 3 and 4, the support members 20 comprises a doughnut-shaped support plate 20a rotatably attached to the cylindrical portion 31b of the stationary drum 31 through a bearing B4, and a rail 20b attached onto a surface of the support plate 20a facing the distal end side, along an outer peripheral edge of the support plate 20a. The support plate 20a is provided on the distal end side (left side in FIGS. 3 and 4) with respect to the turning cam 33. The rail 20b is provided along a circular path about the rotation axis C.

Similarly, the support members 21 comprises a doughnut-shaped support plate 21a rotatably attached to the cylindrical portion 31b of the stationary drum 31 through a bearing B5, and a rail 21b attached onto a surface of the support plate 21a facing the distal end side, along an outer peripheral edge of the support plate 21a. The support plate 21a is provided on the proximal end side (right side in FIGS. 3 and 4) with respect to the turning cam 33. The rail 21b is provided along a circular path about the rotation axis C.

The rails 20b, 21b of the support members 20, 21 are engaged, respectively, with the aftermentioned sliders 26d, 26e provided in the holding mechanism 19. Thus, the holding mechanism 19 is permitted to move along the circular path defined by the rails 20b, 21b, and restricted from moving in any other direction.

Therefore, when the rotary shaft 15 is rotated and thereby an angle of the arm 17 with respect to the rotary supporting body 16 is changed, the holding mechanism 19 coupled to the arm 17 through the link lever 18 is moved with respect to the rotary shaft 15 along the circular path defined by the rails 20b, 21b. As a result, the angular speed of the holding mechanism 19 is changed.

Specifically, in FIG. 2, when the rotary shaft 15 is rotated about the rotation axis C in a clockwise direction, the cam follower 17d is guided along the cam groove 32b. Thus, the arm 17 connected to one of the holding mechanisms 19 currently located, e.g., at a receiving position for receiving the absorbent body A from the transfer roller 5, will be gradually inclined in the rotation direction of the rotary shaft 15 with respect to the rotary supporting body 16 (an interior angle between the arm 17 and the link lever 18 will be gradually narrowed). As a result, the holding mechanism 19 is pulled by the link lever 18 in the rotation direction with respect to the rotary supporting body 16 (rotary shaft 15), i.e., the holding mechanism 19 is accelerated. This acceleration period continues until just before a transfer position for transferring the absorbent body A to the two sheets S1, S2 located between the conveying device 10 and the receiving roller 6, and, in a zone from this position to the transfer position, the holding mechanism 19 is revolved at a constant speed.

When the rotary shaft 15 is further rotated, the arm 17 connected to the holding mechanism 19 currently located at the transfer position will be gradually inclined in a direction opposite to the rotation direction with respect to the rotary supporting body 16 (the interior angle between the arm 17 and the link lever 18 will be gradually widened). As a result, the holding mechanism 19 is pushed by the link lever 18 in the direction opposite to in the rotation direction with respect to the rotary supporting body 16 (rotary shaft 15), i.e., the holding mechanism 19 is decelerated. This deceleration period continues until just before the receiving position, and, in a zone from this position to the receiving position, the holding mechanism 19 is revolved at a constant speed.

As above, in this embodiment, the speed-changing cam 32, the arm 17 and the link lever 10 are correspond to a speed-changing mechanism for changing the angular speed of each of the ten holding mechanisms 19 such that an angular difference arises between mutually adjacent two of the ten holding mechanisms 19.

Further, each of the holding mechanisms 19 is configured to hold the absorbent body A transferred from the transfer roller 5, and, after turning the absorbent body A 90 degrees, transfer the absorbent body A to the two sheets S1, S2 located between each of the holding mechanisms 19 and the receiving roller 6.

Specifically, as depicted in FIGS. 2 to 4, each of the holding mechanisms 19 comprises: a drive base 26 connected on the speed-changing mechanism; a holding pad 27 attached to the drive base 26 through a turning shaft 28; a lever 29 attached to the turning shaft 28; a cam follower (turning cam follower) 30 attached to the lever 29.

The drive base 26 comprises: an outer wall 26a provided outside the turning cam 33, the support members 20, 21, the arm 17 and the link lever 18 in a radial direction of the rotary shaft 15 (a direction orthogonal to the rotation axis C); two supported portions 26b, 26c each protruding from the outer wall 26a inwardly in the radial direction; two sliders 26d, 26e provided, respectively, to the supported portions 26b, 26c. The link lever 18 is rotatably attached to a distal-facing surface of the distal-end-side supported portion 26b through the pivot 18b. Further, the slider 26d is provided on a proximal-facing surface of the supported portion 26b and engaged with the rail 20b as mentioned above. On the other hand, the slider 26e is provided on a proximal-facing surface of the proximal-end-side supported portion 26c, and engaged with the rail 21b as mentioned above.

The holding pad 27 has a holding surface facing outwardly in the radial direction of the rotary shaft 15 and capable of holding the absorbent body A. Specifically, the holding surface of the holding pad 27 is formed with a suction hole whose depiction is omitted is formed. Air outside the holding surface can be suctioned via the suction hole, so as to enable the suction body A to be suction-held on the holding surface. Here, although the holding surface of the holding pad 27 in FIG. 2 is formed in a flat shape, the shape of the holding surface is not particularly limited.

The turning shaft 28 extends from the holding pad 27 inwardly in the radial direction of the rotary shaft 15, and penetrates through the outer wall 26a of the drive base 26. Further, the turning shaft 28 is supported by the outer wall 26a in a manner rotatable about an axis along the radial direction of the rotary shaft 15.

The lever 29 is fixed to an inward end of the turning shaft 28 in the radial direction of the rotary shaft 15. Further, the lever 29 extends in a direction orthogonal to the rotation axis of the turning shaft 28.

The cam follower 30 is provided at a distal end of the lever 29 in a manner rotatable about an axis parallel to the turning shaft 28. The rotation axes of the turning shaft 28 and the cam follower 30 are provided, respectively, at different positions on a plane orthogonal to the turning shaft 28. Further, the cam follower 30 extends from the lever 29 inwardly in the radial direction of the rotary shaft 15, and is engaged with the cam groove 33b of the turning cam 33.

Thus, according to rotation of the rotary shaft 15, the cam follower 30 is guided along an inner surface (turning guide surface) of the cam groove 33b. Specifically, the cam follower 30 is guided by the cam groove 33b such that the holding pad 27 can be turned about the turning shaft 28 according to revolution of the holding mechanism 19 about the rotary shaft 15. As a result, the absorbent body A held by the holding pad 27 is turned 90 degrees during a period of time when it is conveyed from the transfer roller 5 to the receiving roller 6.

In the conveying device 10 configured as above, the magnitude of a gap between mutually adjacent two of the holding mechanisms 19 is changed by the aforementioned speed-changing mechanism (the speed-changing cam 32, the arm 17 and the link lever 18). In this embodiment, the turning cam 33 is provided in the gap between the two holding mechanisms 19. Thus, if foreign matter such as mote or dust intrudes into the gap from an outside thereof in the radial direction of the rotary shaft 15, the foreign matter is likely to be stuck between the cam follower 30 and the cam groove 33b, leading to abnormality in turning operation of the holding pad 27.

Figure 5:
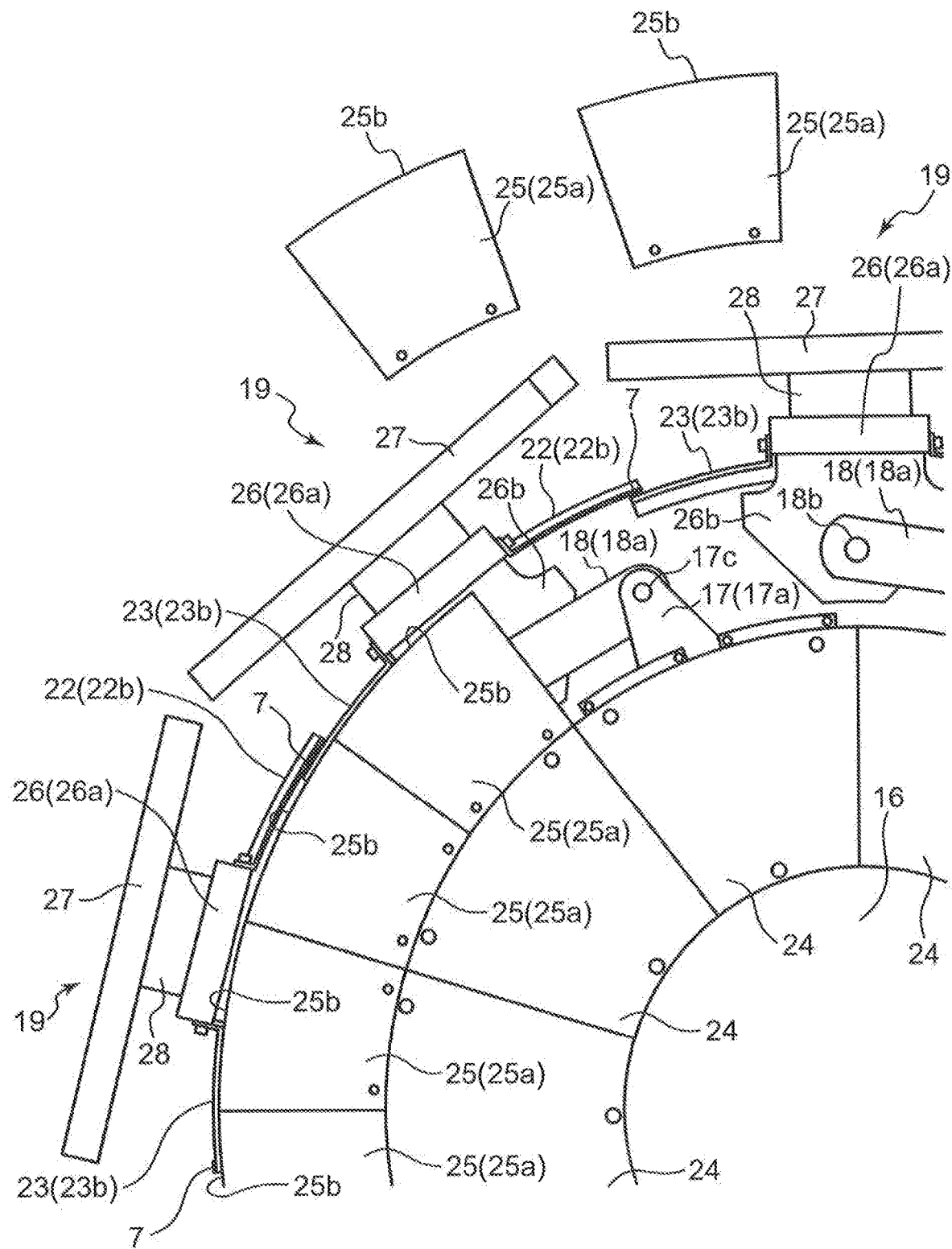
FIG. 5 is a front view enlargedly depicting a part of the conveying device in FIG. 2.
Figure 6:
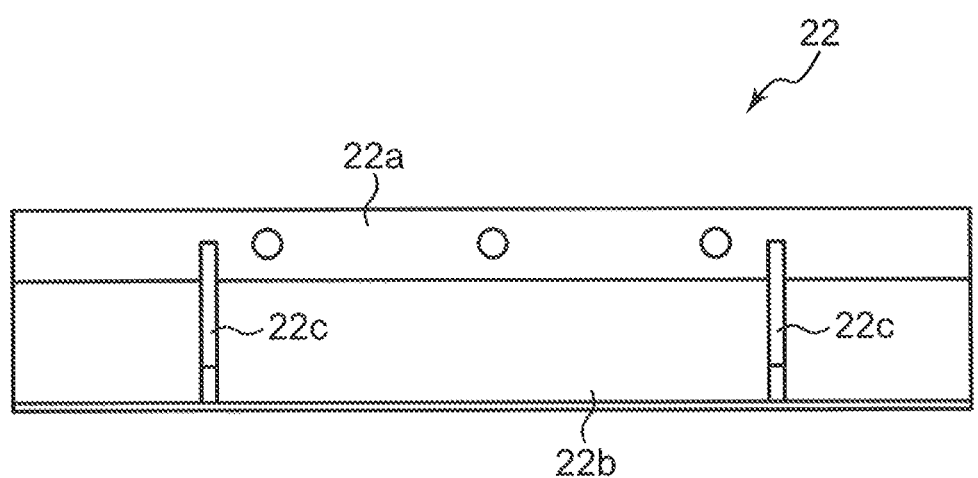
FIG. 6 is a side view of a first cover in FIG. 5.
Figure 7:
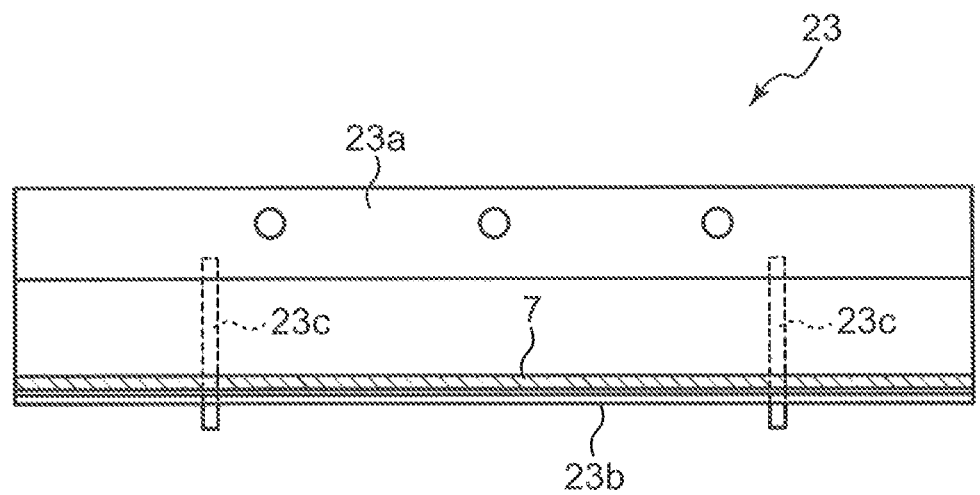
FIG. 7 is a side view of a second cover in FIG. 5.

Therefore, as depicted in FIGS. 5 to 7, the conveying device 10 comprises a first cover 22 extending from a first holding mechanism which is one of mutually adjacent two of the ten holding mechanisms 19, toward a second holding mechanism which is a remaining one of the two holding mechanisms 19, and a second cover 23 extending from the second holding mechanism toward the first holding mechanism. The gap between the two holding mechanisms 19 are covered from the outside thereof in the radial direction of the rotary shaft 15 by the two covers 22, 23.

In this embodiment, each of the ten holding mechanisms 19 has the first cover 22 and the second cover 23. The ten sets of the first cover 22 and the second cover 23 have the same configuration. Thus, the following description will be made about only one set of the first cover 22 and the second cover 23.

Specifically, the first cover 22 has: an attaching portion 22a attached to the outer wall 26a of the drive base 26 of the first holding mechanism; a cover portion 22b extending from the attaching portion 22a toward the second holding mechanism; a reinforcing rib 22c provided to extend over the attaching portion 22a and the cover portion 22b.

Similarly, the second cover 23 has: an attaching portion 23a attached to the outer wall 26a of the drive base 26 of the second holding mechanism; a cover portion 23b extending from the attaching portion 22a toward the first holding mechanism; a reinforcing rib 23c provided to extend over the attaching portion 23a and the cover portion 23b.

The cover portion 22b of the first cover 22 and the cover portion 23b of the second cover 23 have respective lengths enough to overlap with each other in the radial direction of the rotary shaft 15, in a state in which the mutually adjacent two holding mechanisms 19 are furthest apart from each other. Specifically, the cover portion 22b is overlapingly disposed outside the cover portion 23b in the radial direction of the rotary shaft 15.

Further, the cover portion 22b of the first cover 22 and the cover portion 23b of the second cover 23 are spaced apart from each other in the radial direction of the rotary shaft 15. This makes it possible to prevent the occurrence of sliding resistance between the cover portions 22b, 23b when the two holding mechanisms 19 move close to or move away from each other.

On the other hand, if the cover portions 22b, 23b are spaced apart from each other in the radial direction of the rotary shaft 15, foreign matter is likely to intrude from between the cover portions 22b, 23b. Therefore, in order to prevent the intrusion of foreign matter, the rotary mechanism 12 of the conveying mechanism 10 comprises an interposition member 7 (a member indicated by hatching in FIG. 7) interposed between the two covers 22b, 23b in the radial direction of the rotary shaft 15.

The interposition member 7 is provided only between respective regions of the first cover 22 and the second cover which overlap with each other in the radial direction in the state in which the mutually adjacent two holding mechanisms 19 are furthest apart from each other. Specifically, as depicted in FIG. 7, the interposition member 7 is provided only on a distal end (end closer to the first holding mechanisms) of the cover portion 23b of the second cover 23. This makes it possible to prevent the intrusion of foreign matter while preventing the occurrence of the sliding resistance. The interposition member 7 may be formed of, e.g., felt.

As depicted in FIG. 3, the outer wall 26a of the holding mechanism 19 to which the two covers 22, 23 are attached is disposed to cover the cam groove 33b from an outside thereof in the radial direction of the rotary shaft 15. Therefore, the entire cam groove 33b is covered from the outside thereof in the radial direction of the rotary shaft 15 by all of the ten holding mechanisms 19 and all of the ten sets of the first cover 22 and the second cover 23.

Referring to FIGS. 3 and 4, the aforementioned pair of support members 20, 21 are correspond to a pair of covering members provided, respectively, on both sides of the turning cam 33 in an axial direction of the rotary shaft 15, to form a covered chamber R1 covered from an outside thereof in the radial direction of the rotary shaft 15 and both sides thereof in the axial direction of the rotary shaft 15, in cooperation with all of the ten holding mechanisms 19 and all of the ten sets of the first cover 22 and the second cover 23.

Specifically, the support member 21 comprises an outer peripheral cover 21c covering a gap between the support plate 21a and the drive base 26 of the holding mechanism 19 from an outside thereof in the radial direction of the rotary shaft 15. The outer peripheral cover 21c is provided along the outer peripheral edge of the support plate 21a over the entire circumference about the rotary shaft 15. The covered chamber R1 is defined by the support plate 20a of the support member 20, the support plate 21a and the outer peripheral cover 21c of the support member 21, the drive base 26, the first cover 22, and the second cover 23.

Further, the cam groove 33b of the turning cam 33 is provided within the covered chamber R1.

The support member 20 also comprises an outer peripheral cover 20c covering a gap between the support plate 20a and the supported portion 26b from an outside thereof in the axial radial direction of the rotary shaft 15. The outer peripheral cover 20c and the outer peripheral cover 21c cover the rails 20b, 21b, and the sliders 26d, 26e, respectively, from an outside thereof in the radial direction of the rotary shaft 15.

As depicted in FIG. 3, each of the first cover 22 and the second cover 23 is provided to extend over a region between the position of a proximal-facing edge face of the outer periphery cover 20c and the position of a distal-facing edge face of the outer periphery cover 21c, in the axial direction of the rotary shaft 15.

Here, since the holding mechanisms 19 are revolved, respectively, at different angular speeds, each of the support members 20, 21 provided on opposite sides of the holding mechanisms in the axial direction is permitted to be relatively displaced with respect to the ten holding mechanisms 19 and the ten sets of the two covers 22, 23 in a revolution direction about the rotary shaft 15, by the rail 20b, 21b and the slider 26d, 26e. In this case, however, a clearance needs to provide between each of the support members 20, 21 and each of the ten holding mechanisms 19 and the ten sets of the two covers 22, 23 so as to permit the relative displacement therebetween, and it is difficult to prevent intrusion of foreign matter through this clearance.

Therefore, as depicted in FIG. 4, the stationary drum 31 of the conveying device 10 is provided with a filter 31e for trapping foreign matter, and a fan (external air introduction means) 31c capable of introducing external air into the covered chamber R1 via the filter 31e as an arrow shown in FIG. 4. The filter 31e and the fan 31c are provided within a through-hole 31d formed in the bottom plate portion 31a. The through-hole 31d is opened to a space inside the cylindrical portion 31b. Thus, upon activation of the fan 31c, air is introduced into the space inside the cylindrical portion 31b via the through-hole 31d, and further introduced into the covered chamber R1 via a hole (indicated by the two-dot chain line in FIG. 4; its reference sign is omitted) formed in the cylindrical portion 31b. Thus, even in the case where the above clearance is formed, it becomes possible to discharge air via the clearance to thereby prevent intrusion of foreign matter into the covered chamber R1.

Further, air introduced into the space inside the cylindrical portion 31b of the stationary drum 31 by the fan 31c passes through the vicinities of the bearings B4, B5 rotatably supporting the support members 20, 21 with respect to the cylindrical portion 31b, so that it is possible to cool these bearings B4, B5. This also makes it possible to suppress thermal expansion of (outer and inner races of) the bearings B4, B5 due to a temperature raise of the bearings B4, B5 to achieve stabilization in operation of the holding mechanisms 19.

As mentioned above, the speed-changing mechanism (the speed-changing cam 32, the arm 17 and the link lever 18) is provided on the distal end side (left side in FIG. 4) with respect to the distal-end-side support member 20, i.e., provided outside the covered chamber R1 in the axial direction of the rotary shaft 15 (on the left side in FIG. 4) with respect to the covered chamber R1).

Further, as depicted in FIGS. 3 to 5, the rotary mechanism 12 of the conveying device 10 comprises a rotary shaft-side cover (its reference sign is omitted) which covers the speed-changing mechanism from one side thereof opposite to the covered chamber R1 in the axial direction of the rotary shaft 15 and an outside thereof in the radial direction of the rotary shaft 15, wherein the rotary shaft-side cover is fixed to the rotary shaft 15.

The rotary shaft-side cover comprises a plurality of sector-shaped inner covers 24 arranged along the outer peripheral edge of the rotary supporting body 16 and each fixed to the outer peripheral edge of the rotary supporting body 16, and two outer covers 25 detachably attached to an outer peripheral edge of each of the inner covers 24.

Each of the inner covers 24 is a plate member extending along a plane orthogonal to the rotation axis C, and covers the speed-changing mechanism, particularly the arm 17 and the speed-changing cam 32, from a direction parallel to the axial direction of the rotary shaft 15.

Each of the two outer covers 25 is a plate member having a sidewall portion 25a extending from the outer peripheral edge of the inner cover 24 outwardly in the radial direction of the rotary shaft 15, and a peripheral wall portion 25b extending from an outer peripheral edge of the sidewall portion 25a toward the proximal side (right side in FIG. 4) in the axial direction of the rotary shaft 15. The sidewall portion 25a extends along the plane orthogonal to the rotation axis C, and covers the speed-changing mechanism, particularly the arm 17 and the link lever 18, from the direction parallel to the axial direction of the rotary shaft 15. The peripheral wall portion 25b extends along an arc plane about the rotation axis C, and covers the speed-changing mechanism, particularly the arm 17 and the link lever 18, from an outside thereof in the radial direction of the rotary shaft 15.

Referring to FIG. 4, the drive mechanism 4 comprises: a motor 34; a drive shaft 35 configured to be rotationally driven by the motor 34; a shaft-side drive pulley 36 fixed to the drive shaft 35; a shaft-side driven pulley 37 fixed to the rotary shaft 15; and a belt (its reference sign is omitted) indicated by the two dot chain line and wound around between the shaft-side drive pulley 36 and the shaft-side drive pulley 37. When the drive shaft 35 is rotated by the motor 34, a driving force of the motor 34 is transmitted to the rotary shaft 15 via the belt.

Here, the support members 20, 21 may be fixed (may be fixed to the supporting plate 11) in spite of a rotation of the rotary shaft 15, because the support members 20, 21 are provided as a means to rotatably support the ten holding mechanisms 19. However, the ten holding mechanisms 19 are revolved, respectively, at different speeds, as mentioned above. Thus, if the support members 20, 21 are fixed, forces having different vectors are simultaneously applied to each of the support members 20, 21 along with revolution of the ten holding mechanisms 19, so that a resulting reaction force concentrates on the speed-changing cam 32 and the cam follower 17d, leading to degradation of the speed-changing cam 32 and the cam follower 17d.

Therefore, the drive mechanism 14 is operable to rotationally drive the two support members 20, 21 in synchronization with the rotary shaft 15.

Specifically, the drive mechanism 14 further comprises: a support-side drive pulley 38 fixed to a shaft (its reference sign is omitted) coupled to the drive shaft 35 via non-depicted pulleys and a non-depicted belt; a support-side driven pulley 39 fixed to the support plate 21a of the proximal end-side support member 21; and a belt (its reference sign is omitted) wound around between the support-side drive pulley 38 and the support-side driven pulley 39. When the drive shaft 35 is rotated by the motor 34, a driving force of the motor 34 is transmitted to the support member 21 via the belt.

The drive mechanism 14 further comprises an angled member 26f connecting the rotary supporting body 16 and the support plate 20a of the front-side support member 20 together. Thus, a driving force of the motor 34 is transmitted to the support member 20 via the rotary shaft 15 and the rotary supporting body 16.

In this way, the two support members 20, 21 are rotationally driven in synchronization with the rotary shaft 15, so that a force to be applied to the two support members 20, 21 is reduced to a force corresponding to a difference among relative speeds of the ten holding mechanisms 19 with respect to the rotary shaft 15, to reduce the degradation of the speed-changing cam 32 and the cam follower 17d.

As described above, the first cover and the second cover extending, respectively, from mutually adjacent two of the ten holding mechanisms 19 overlap with each other in the radial direction. Thus, differently from the conventional accordion-shaped cover deformable in response to a change in distance between the two holding mechanisms 19, it is possible to cover the gap between the two holding mechanisms 19 from the outside thereof in the radial direction, while maintaining the shape of the first cover 22 and the second cover 23.

Further, the two covers 22, 23 have respective lengths enough to be able to overlap with each other in the radial direction, in a state in which the two holding mechanisms 19 are furthest apart from each other. It is possible to prevent foreign matter from entering into the gap between the two holding mechanisms 19, even if the distance between the two holding mechanisms 19 is changed.

Thus, it is possible to more effectively prevent foreign matter from entering in between mutually adjacent two of the ten holding mechanisms 19, irrespective of a distance between the two holding mechanisms 19.

The above embodiment can further bring out the following advantageous effects.

The two covers 22, 23 are spaced apart from each other in the radial direction of the rotary shaft. This makes it possible to prevent a sliding movement between the two covers 22, 23 along with a relative displacement between the two holding mechanisms 19, to ease wear of the two covers 22, 23.

The interposition member 7 interposed between the two covers 22, 23 in the radial direction is provided only between respective regions of the two covers 22, 23 which overlap with each other in the radial direction in the state in which the two holding mechanisms 19 are furthest apart from each other. Thus, it is possible to minimally suppress an increase in sliding resistance caused by providing the interposition member 7, while preventing foreign matter from intruding through the gap between the two covers 22, 23.

The entire cam groove (turning guide surface) 33b can be covered from the outside thereof in the radial direction of the rotary shaft 15 by the ten holding mechanisms 19 and the ten sets of the two covers 22, 23, so that it is possible to reliably prevent foreign matter from intruding in between the cam follower 30 and the cam groove 33b.

The cam groove 33b can be additionally covered from both sides thereof in the axial direction of the rotary shaft 15 by the pair of support members (covering members) 20, 21, so that it is possible to reliably prevent foreign matter from intruding in between the cam groove 33b and the cam follower 30 along the axial direction.

In this embodiment, external air passing through the filter 31e can be introduced into the covered chamber R1. Thus, even in the case where a clearance is formed between each of the support members 20, 21 and each of the ten holding mechanisms 19 and the ten sets of the two covers 22, 23, it is possible to discharge air inside the covered chamber R1, through the clearance, to thereby prevent foreign matter from intruding into the covered chamber R1 through the clearance.

The speed-changing mechanism (the speed-changing cam 32, the arm 17 and the link lever 18) can be covered from one side thereof opposite to the covered chamber R1 in the axial direction (one side thereof in the axial direction) and the outside thereof in the radial direction, by the rotary shaft-side cover (the inner covers 24 and the outer covers 25). Further, the support member 20 exists on the other side of the speed-changing mechanism opposite to the rotary shaft-side cover in the axial direction of the rotary shaft 15, so that it is possible to additionally cover the speed-changing mechanism from the other side thereof in the axial direction by the support member 20. This makes it possible to suppress the occurrence of abnormality in operation of the speed-changing mechanism due to adherence of foreign matter to the speed-changing mechanism.

Further, the rotary shaft-side cover is fixed to the rotary shaft 15, so that it is possible to achieve weight reduction of the holding mechanisms 19 to thereby improve the conveyance speed of the absorbent body A.

In the above manner, defective operation of the conveying device 10 can be suppressed. Thus, when this conveying device 10 is used for manufacturing of a disposable diaper 1, it becomes possible to improve efficiency of manufacturing of the disposable diaper 1.

It should be noted that the present invention is not limited to the above embodiment. For example, the following embodiments may be employed.

Although the above embodiment has been described based on an example in which the two covers 22, 23 is spaced apart from each other in the radial direction of the rotary shaft 15, the two covers 22, 23 may be in contact with each other in the radial direction. In this case, the interposition member 7 can be omitted.

Although the above embodiment has been described based on an example in which the entire cam groove (turning guide surface) 33b is covered from the outside thereof in the radial direction of the rotary shaft by the ten holding mechanism 19 and the ten sets of the two covers 22, 23, at least part of the cam groove 33b may be covered from the outside thereof in the radial direction of the rotary shaft by the ten sets of the two covers 22, 23. In this case, it is possible to reduce a negative influence of foreign matter on the turning operation of the holding pads 27.

Although the above embodiment has been described based on an example in which the cam groove 33b is covered from both sides thereof in the axial direction of the rotary shaft 15 by the support members (pair of covering members) 20, 21, at least one of the support members 20, 21 may be omitted.

Although the above embodiment has been described based on an example in which the filter 31e and the fan 31c are provided, they may be omitted.

Although the above embodiment has been described based on an example in which the speed-changing mechanism (the speed-changing cam 32, the arm 17 and the link lever 18) is disposed outside the covered chamber R1, the speed-changing mechanism may be provided inside the covered chamber R1. In this case, the rotary shaft-side cover (the inner covers 24 and the outer covers 25) may be omitted.

In the above embodiment, the fan 31c is shown as one example of the external air introduction means. However, the external air introduction means is not limited to the fan 31c. For example, a blower (compressor, etc.) capable of sending air into the covered chamber R1 through the filter 31e may be employed as the external air introduction means. When a compressor is employed as the external air introduction means, it is preferable to dehumidify air sent from the compressor.

A positional relationship between the first cover 22 and the second cover 23 may be inverted with respect to the holding mechanism 19, in the revolution direction about the rotary shaft 15. Further, although the above embodiment has been described based on an example in which the cover portion 22b of the first cover 22 is overlapingly disposed outside the cover portion 23b of the second cover 23 in the radial direction, the cover portion 23b may be overlapingly disposed outside the cover portion 22b in the radial direction. In this case, the interposition member 7 is preferably provided between the cover portion 22b and the cover portion 23b.

The above specific embodiments mainly include the inventions having the following features.

The present invention provides a conveying device for conveying a conveyance target member to be conveyed. The conveying device comprises: a rotary shaft; a plurality of holding mechanisms attached to the rotary shaft in a manner rotatable in response to rotation of the rotary shaft and each capable of holding the conveyance target member, wherein the plurality of holding mechanisms are arranged at respective positions having different angles about the rotary shaft; a speed-changing mechanism which changes an angular speed of each of the plurality of holding mechanisms such that an angular difference arises between mutually adjacent two of the plurality of holding mechanisms; a first cover extending from a first holding mechanism which is one of the two holding mechanisms, toward a second holding mechanism which is a remaining one of the two holding mechanisms, such that the first cover covers a gap between the two holding mechanisms from an outside thereof in a radial direction of the rotating shaft; and a second cover extending from the second holding mechanism toward the first holding mechanism such that the second cover covers the gap from the outside thereof in the radial direction, and overlapping with the first cover in the radial direction, wherein the first cover and the second cover have respective lengths enough to be able to overlap with each other in the radial direction, in a state in which the two holding mechanisms are furthest apart from each other.

In the conveying device of the present invention, the first cover and the second cover extending, respectively, from mutually adjacent two of the plurality of holding mechanisms overlap with each other in the radial direction. Thus, differently from the conventional accordion-shaped cover deformable in response to a change in distance between the two holding mechanisms, it is possible to cover the gap between the two holding mechanisms from the outside thereof in the radial direction, while maintaining the shape of the first cover and the second cover.

Further, in the present invention, the two covers have respective lengths enough to be able to overlap with each other in the radial direction, in a state in which the two holding mechanisms are furthest apart from each other. It is possible to prevent foreign matter from entering into the gap between the two holding mechanisms, even if the distance between the two holding mechanisms is changed.

Thus, in the present invention, it is possible to more effectively prevent foreign matter from entering in between mutually adjacent two of the ten holding mechanisms, irrespective of a distance between the two holding mechanisms.

Here, the first cover and the second cover may be in contact with each other in the radial direction. In this case, however, the two covers are rubbed against each other due to a change in distance between the two holding mechanisms, leading to large wear of the two covers.

Considering this, preferably, in the conveying device of the present invention, the first cover and the second cover are spaced apart from each other in the radial direction.

According to this feature, it is possible to prevent a sliding movement between the two covers along with a relative displacement between the two holding mechanisms, to ease wear of the two covers.

Here, in the above case where the two covers are spaced apart from each other in the radial direction, foreign matter is likely to intrude in between the two holding mechanisms through a gap between the two covers.

Considering this, preferably, the above conveying device further comprises an interposition member interposed between the first cover and the second cover in the radial direction, wherein the interposition member is provided only between respective regions of the first cover and the second cover which overlap with each other in the radial direction in the state in which the two holding mechanisms are furthest apart from each other.

According to this feature, the interposition member interposed between the two covers in the radial direction is provided only between respective regions of the two covers which overlap with each other in the radial direction in the state in which the two holding mechanisms are furthest apart from each other. Thus, it is possible to minimally suppress an increase in sliding resistance caused by providing the interposition member, while preventing foreign matter from intruding through the gap between the two covers.

Here, each of the plurality of holding mechanisms may comprise: a holding pad which holds the conveyance target member; a turning shaft extending from the holding pad inwardly in the radial direction; and a turning cam follower attached to the turning shaft, wherein the conveying device further comprises a turning cam having a turning guide surface which guides the turning cam follower such that the holding pad can be turned about the turning shaft in response to revolution of the plurality of holding mechanisms about the rotary shaft. In this case, it becomes possible to turn the conveyance target member held by the holding pad, about the turning shaft, while conveying the conveyance target member about the rotary shaft.

In this case, however, if foreign matter intrudes in between the turning cam follower and the turning guide surface, it becomes impossible to accurately guide the turning cam follower.

Considering this, preferably, in the above conveying device, the turning guide surface has a portion covered from an outside thereof in the radial direction by the first cover and the second cover.

According to this feature, the turning guide surface can be covered from the outside thereof in the radial direction by the two covers, so that it is possible to suppress intrusion of foreign matter in between the turning cam follower and the turning guide surface.

Particularly preferably, all of the plurality of holding mechanisms are provided, respectively, with a plurality of sets of the first cover and the second cover, wherein the entire turning guide surface is covered from an outside thereof in the radial direction by all of the plurality of holding mechanisms and all of the plurality of sets of the first cover and the second cover.

According to this feature, the entire turning guide surface can be covered from the outside thereof in the radial direction by all of the plurality of holding mechanisms and all of the plurality of sets of the two covers, so that it is possible to reliably prevent foreign matter from intruding in between the cam follower and the turning guide surface, Here, if the turning guide surface is covered from only the outside thereof in the radial direction, foreign matter is likely to intrude in between the turning cam and an assembly of the holding mechanism and the first and second covers, along the axial direction of the rotary shaft.

Considering this, preferably, the above conveying device further comprises a pair of covering members provided, respectively, on both sides of the turning cam in an axial direction of the rotary shaft, to form a covered chamber covered from an outside thereof in the radial direction and both sides thereof in the axial direction, in cooperation with all of the plurality of holding mechanisms and all of the plurality of sets of the first cover and the second cover, wherein the turning guide surface is provided within the covered chamber.

According to this feature, the turning guide surface can be additionally covered from both sides thereof in the axial direction by the pair of covering members, so that it is possible to reliably prevent foreign matter from intruding in between the turning guide surface and the cam follower along the axial direction.

Here, since the plurality of holding mechanisms are revolved, respectively, at different angular speeds, each of the pair of covering members provided on opposite sides of the holding mechanisms in the axial direction is permitted to be relatively displaced with respect to the plurality of holding mechanisms and the plurality of sets of the first and second covers in a revolution direction about the rotary shaft. In this case, however, a clearance needs to provide between each of the covering members and each of the plurality of holding mechanisms and the plurality of sets of the first and second covers so as to permit the relative displacement therebetween, and it is difficult to prevent intrusion of foreign matter through this clearance.

Considering this, preferably, the above conveying device further comprises: a filter for trapping foreign matter; and an external air introduction means capable of introducing external air into the covered chamber via the filter.

According to this feature, external air passing through the filter can be introduced into the covered chamber. Thus, even in the case where the above clearance is formed, it becomes possible to discharge air inside the covered chamber, through the clearance, to thereby prevent foreign matter from intruding into the covered chamber through the clearance.

Here, although the speed-changing mechanism may be provided inside the covered chamber, there is a situation where the speed-changing mechanism has to be provided outside the covered chamber in the axial direction due to a structure of the conveying device.

In this case, preferably, the above conveying device further comprises a rotary shaft-side cover which covers the speed-changing mechanism from one side thereof opposite to the covered chamber in the axial direction and an outside thereof in the radial direction, wherein the rotary shaft-side cover is fixed to the rotary shaft.

According to this feature, the speed-changing mechanism provided outside the covered chamber can be covered from one side thereof opposite to the covered chamber in the axial direction (one side thereof in the axial direction) and the outside thereof in the radial direction, by the rotary shaft-side cover. Further, one of the covering members exists on the other side of the speed-changing mechanism opposite to the rotary shaft-side cover in the axial direction, so that it is possible to additionally cover the speed-changing mechanism from the other side thereof in the radial direction by the covering member. This makes it possible to suppress the occurrence of abnormality in operation of the speed-changing mechanism due to adherence of foreign matter to the speed-changing mechanism.

Further, the rotary shaft-side cover is fixed to the rotary shaft, so that it is possible to achieve weight reduction of the holding mechanisms to thereby improve the conveyance speed of the conveyance target member.

The present invention further provides a method for manufacturing a disposable wearable article having a waist portion to be disposed around a waist region of a wearer and a crotch portion to be disposed on a crotch region of the wearer, using the above conveying device. The method comprises: a waist sheet conveying step of conveying a waist sheet for forming the waist portion, in a longitudinal direction thereof; a crotch member bonding step of conveying a crotch member to the waist sheet, using the conveying device, such that the crotch member is provided in an area of the waist sheet corresponding to the crotch portion, and bonding the crotch member to the waist sheet to form a bonded body; a half-folding step of folding the bonded body in half, in a width direction orthogonal to the longitudinal direction; a side seal forming step of bonding, together, each of two sets of superimposed areas of the waist sheet located, respectively, on both sides of the crotch member in the longitudinal direction, to form a side seal; and a cutting step of cutting the waist sheet such that the side seal is left on each of the both sides of the crotch member in the longitudinal direction, to form the disposable wearable article.

In the manufacturing method of the present invention, the crotch member can be conveyed to the waist sheet by using the conveying device capable of preventing foreign matter from intruding in the gap between the two holding mechanisms in the above manner.

Then, the crotch member is bonded to the waist sheet to form a bonded body, and the bonded body is folded in half, whereafter a side seal is formed in the bonded body, and the waist sheet is cut so as to form the disposable wearable article.

Therefore, the manufacturing method of the present invention makes it possible to suppress defective operation of the conveying device. Thus, when this conveying device is used for manufacturing of a disposable wearable article, it becomes possible to improve efficiency of manufacturing of the disposable wearable article.

The invention claimed is:

1. A conveying device for conveying a conveyance target member to be conveyed, comprising:
    a rotary shaft;
    a plurality of holding mechanisms attached to the rotary shaft in a manner rotatable in response to rotation of the rotary shaft and each capable of holding the conveyance target member, wherein the plurality of holding mechanisms are arranged along a circumference of the rotary shaft at respective positions having different angles about the rotary shaft;
    a speed-changing mechanism which changes an angular speed of each of the plurality of holding mechanisms such that an angular difference arises between mutually adjacent two of the plurality of holding mechanisms;
    a first cover attached to a first holding mechanism which is one of the adjacent two holding mechanisms, such that the first cover covers a circumferential gap between the adjacent two holding mechanisms from an outside thereof in a radial direction of the rotating shaft, the first cover moving in a first circumferential direction together with the first holding mechanism; and
    a second cover attached to a second holding mechanism which is the other one of the adjacent two holding mechanisms, such that the second cover covers the circumferential gap from the outside thereof in the radial direction, the second cover overlapping with the first cover in the radial direction and moving in a second circumferential direction together with the second holding mechanism relative to the first cover moving in the first circumferential direction together with the first holding mechanism,
    wherein the first cover and the second cover have respective lengths which are long enough such that the first and second covers are able to overlap with each other in the radial direction, in a state in which the adjacent two holding mechanisms are furthest apart from each other.

2. The conveying device according to claim 1, wherein the first cover and the second cover are spaced apart from each other in the radial direction.

3. The conveying device according to claim 2, which further comprises an interposition member interposed between the first cover and the second cover in the radial direction, wherein the interposition member is provided only between respective regions of the first cover and the second cover which overlap with each other in the radial direction in the state in which the two holding mechanisms are furthest apart from each other.

4. The conveying device according to claim 1, wherein each of the plurality of holding mechanisms comprises:
    a holding pad which holds the conveyance target member;
    a turning shaft extending from the holding pad inwardly in the radial direction; and
    a turning cam follower attached to the turning shaft,
    the conveyance device further comprising a turning cam having a turning guide surface which guides the turning cam follower such that the holding pad can be turned about the turning shaft in response to revolution of the plurality of holding mechanisms about the rotary shaft, wherein the turning guide surface has a portion covered from an outside thereof in the radial direction by the first cover and the second cover.

5. The conveying device according to claim 4, wherein all of the plurality of holding mechanisms are provided, respectively, with a plurality of sets of the first cover and the second cover, and wherein the entire turning guide surface is covered from an outside thereof in the radial direction by all of the plurality of holding mechanisms and all of the plurality of sets of the first cover and the second cover.

6. The conveying device according to claim 5, which further comprises a pair of covering members provided, respectively, on both sides of the turning cam in an axial direction of the rotary shaft, to form a covered chamber covered from an outside thereof in the radial direction and both sides thereof in the axial direction, in cooperation with all of the plurality of holding mechanisms and all of the plurality of sets of the first cover and the second cover,
wherein the turning guide surface is provided within the covered chamber.

7. The conveying device according to claim 6, wherein the pair of covering members are relatively displaceable with respect to the plurality of holding mechanisms and the plurality of sets of the first cover and the second cover, in a revolution direction about the rotary shaft,
further comprising:
a filter for trapping foreign matter; and
an external air introduction means capable of introducing external air into the covered chamber via the filter.

8. The conveying device according to claim 6, wherein the speed-changing mechanism is provided outside the covered chamber in the axial direction,
further comprising a rotary shaft-side cover which covers the speed-changing mechanism from one side thereof opposite to the covered chamber in the axial direction and an outside thereof in the radial direction, wherein the rotary shaft-side cover is fixed to the rotary shaft.

9. A method for manufacturing a disposable wearable article having a waist portion to be disposed around a waist region of a wearer and a crotch portion to be disposed on a crotch region of the wearer, using the conveying device according to claim 1, comprising:
conveying a waist sheet for forming the waist portion, in a longitudinal direction thereof;
conveying a crotch member to the waist sheet, using the conveying device, such that the crotch member is provided in an area of the waist sheet corresponding to the crotch portion, and bonding the crotch member to the waist sheet to form a bonded body;
folding the bonded body in half, in a width direction orthogonal to the longitudinal direction;
bonding, together, each of two sets of superimposed areas of the waist sheet located, respectively, on both sides of the crotch member in the longitudinal direction, to form a side seal; and
cutting the waist sheet such that the side seal is left on each of the both sides of the crotch member in the longitudinal direction, to form the disposable wearable article.

10. A conveying device for conveying a conveyance target member to be conveyed, comprising:
a rotary shaft;
a plurality of holding mechanisms attached to the rotary shaft in a manner rotatable in response to rotation of the rotary shaft and each capable of holding the conveyance target member, wherein the plurality of holding mechanisms are arranged at respective positions having different angles about the rotary shaft;
a speed-changing mechanism which changes an angular speed of each of the plurality of holding mechanisms such that an angular difference arises between mutually adjacent two of the plurality of holding mechanisms;
a first cover extending from a first holding mechanism which is one of the two holding mechanisms, toward a second holding mechanism which is a remaining one of the two holding mechanisms, such that the first cover covers a gap between the two holding mechanisms from an outside thereof in a radial direction of the rotating shaft; and
a second cover extending from the second holding mechanism toward the first holding mechanism such that the second cover covers the gap from the outside thereof in the radial direction, and overlapping with the first cover in the radial direction,
wherein the first cover and the second cover have respective lengths which are long enough such that the first and second covers are able to overlap with each other in the radial direction, in a state in which the two holding mechanisms are furthest apart from each other,
and wherein the first cover and the second cover are spaced apart from each other in the radial direction.

11. The conveying device according to claim 10, which further comprises an interposition member interposed between the first cover and the second cover in the radial direction, wherein the interposition member is provided only between respective regions of the first cover and the second cover which overlap with each other in the radial direction in the state in which the two holding mechanisms are furthest apart from each other.

12. The conveying device according to claim 10, wherein each of the plurality of holding mechanisms comprises:
a holding pad which holds the conveyance target member;
a turning shaft extending from the holding pad inwardly in the radial direction; and
a turning cam follower attached to the turning shaft,
the conveying device further comprising a turning cam having a turning guide surface which guides the turning cam follower such that the holding pad can be turned about the turning shaft in response to revolution of the plurality of holding mechanisms about the rotary shaft,
wherein the turning guide surface has a portion covered from an outside thereof in the radial direction by the first cover and the second cover.

13. The conveying device according to claim 12, wherein all of the plurality of holding mechanisms are provided, respectively, with a plurality of sets of the first cover and the second cover, and wherein the entire turning guide surface is covered from an outside thereof in the radial direction by all of the plurality of holding mechanisms and all of the plurality of sets of the first cover and the second cover.

14. The conveying device according to claim 13, which further comprises a pair of covering members provided, respectively, on both sides of the turning cam in an axial direction of the rotary shaft, to form a covered chamber covered from an outside thereof in the radial direction and both sides thereof in the axial direction, in cooperation with all of the plurality of holding mechanisms and all of the plurality of sets of the first cover and the second cover,
wherein the turning guide surface is provided within the covered chamber.

15. The conveying device according to claim 14, wherein the pair of covering members are relatively displaceable with respect to the plurality of holding mechanisms and the plurality of sets of the first cover and the second cover, in a revolution direction about the rotary shaft, further comprising:

a filter for trapping foreign matter; and an external air introduction means capable of introducing external air into the covered chamber via the filter.

16. The conveying device according to claim 14, wherein the speed-changing mechanism is provided outside the covered chamber in the axial direction, further comprising a rotary shaft-side cover which covers the speed-changing mechanism from one side thereof opposite to the covered chamber in the axial direction and an outside thereof in the radial direction, wherein the rotary shaft-side cover is fixed to the rotary shaft.

17. A method for manufacturing a disposable wearable article having a waist portion to be disposed around a waist region of a wearer and a crotch portion to be disposed on a crotch region of the wearer, using the conveying device according to claim 10, comprising:

conveying a waist sheet for forming the waist portion, in a longitudinal direction thereof;

conveying a crotch member to the waist sheet, using the conveying device, such that the crotch member is provided in an area of the waist sheet corresponding to the crotch portion, and bonding the crotch member to the waist sheet to form a bonded body;

folding the bonded body in half, in a width direction orthogonal to the longitudinal direction;

bonding, together, each of two sets of superimposed areas of the waist sheet located, respectively, on both sides of the crotch member in the longitudinal direction, to form a side seal; and cutting the waist sheet such that the side seal is left on each of the both sides of the crotch member in the longitudinal direction, to form the disposable wearable article.

* * * * *